(12) United States Patent
Nakanishi et al.

(10) Patent No.: US 8,045,781 B2
(45) Date of Patent: Oct. 25, 2011

(54) X-RAY COMPUTED TOMOGRAPHY APPARATUS, RECONSTRUCTION PROCESSING APPARATUS, AND IMAGE PROCESSING APPARATUS

(75) Inventors: Satoru Nakanishi, Utsunomiya (JP); Naruomi Akino, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 756 days.

(21) Appl. No.: 12/169,963

(22) Filed: Jul. 9, 2008

(65) Prior Publication Data
US 2009/0016485 A1 Jan. 15, 2009

(30) Foreign Application Priority Data

Jul. 10, 2007 (JP) ................................. 2007-181308
May 12, 2008 (JP) ................................. 2008-125121

(51) Int. Cl.
*G06K 9/00* (2006.01)
(52) U.S. Cl. ........................... 382/131; 378/19; 378/901
(58) Field of Classification Search .................. 382/128, 382/130–132; 378/4–20, 901
See application file for complete search history.

(56) References Cited

U.S. PATENT DOCUMENTS 6,266,388 B1 7/2001 Hsieh ................................ 378/8
6,546,067 B2 4/2003 Aradate et al.

FOREIGN PATENT DOCUMENTS

CN 1449722 A 10/2003
WO WO 02/086822 A1 10/2002

OTHER PUBLICATIONS

U.S. Appl. No. 12/126,617, filed May 23, 2008, Satoru Nakanishi.
U.S. Appl. No. 12/038,205, filed Feb. 27, 2008, Satoru Nakanishi.
Extended European Search Report issued Dec. 2, 2010, in European Patent Application No. 08012420.9.
Jiang Hsieh, "A Practical Cone Beam Artifact Correction Algorithm", Nuclear Science Symposium Conference Record, vol. 2, XP-010557010, Oct. 15, 2000, pp. 15-71 to 15-74.
Office Action Mailed on Jun. 20, 2011, in European Patent Application No. 11162651.1 filed on Jul. 9, 2008.

*Primary Examiner* — Courtney Thomas
(74) *Attorney, Agent, or Firm* — Oblon, Spivak, McClelland, Maier & Neustadt, L.L.P.

(57) ABSTRACT

An X-ray computed tomography apparatus scans a subject to be examined with cone beam X-rays, and generates reference volume data on the basis of projection data. This apparatus extracts a cone beam artifact component contained in the reference volume data on the basis of the typical shape and direction of the cone beam artifact component. This apparatus generates resultant volume data with the reduced cone beam artifact by subtracting the cone beam artifact component from the reference volume data.

17 Claims, 6 Drawing Sheets

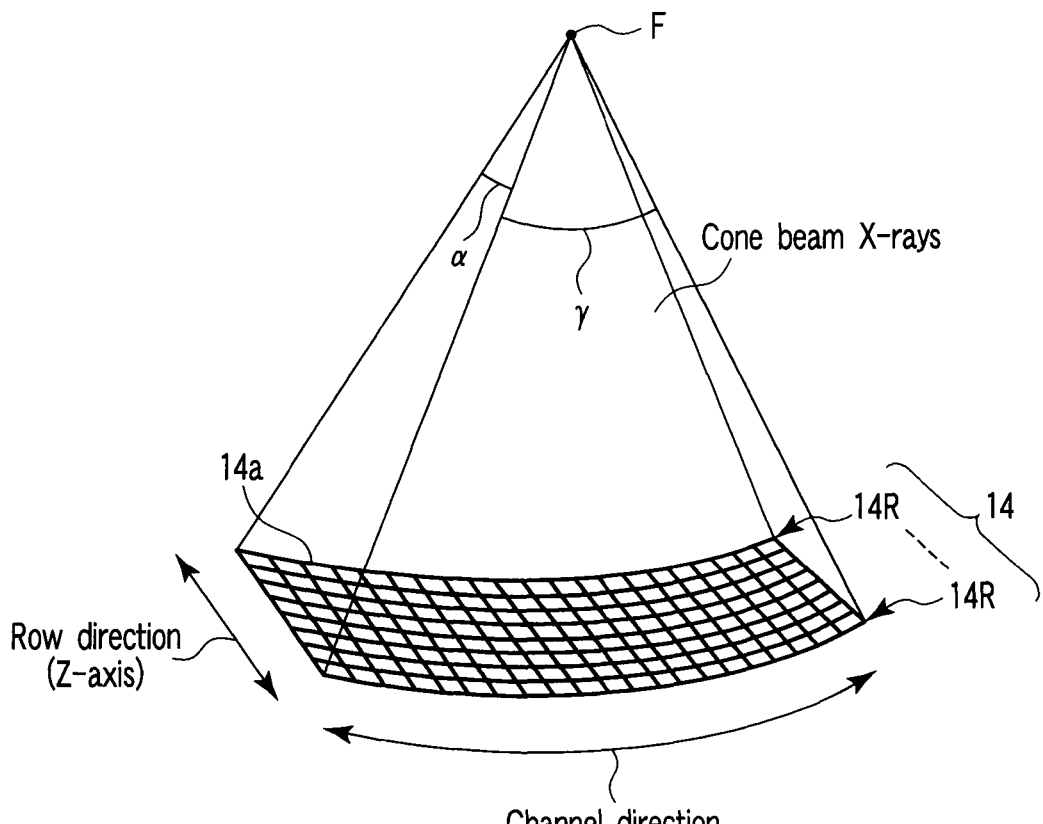
F I G. 2
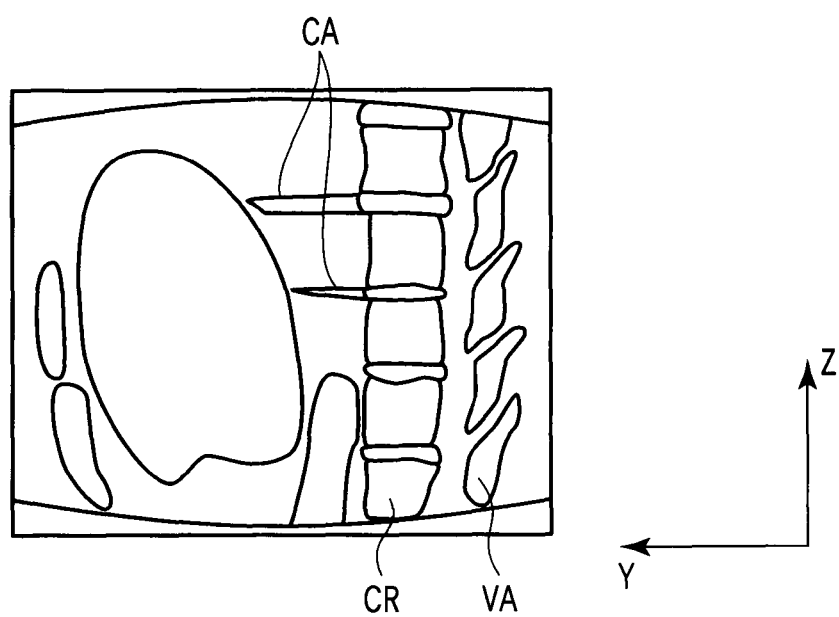
F I G. 3

X-RAY COMPUTED TOMOGRAPHY APPARATUS, RECONSTRUCTION PROCESSING APPARATUS, AND IMAGE PROCESSING APPARATUS

CROSS-REFERENCE TO RELATED APPLICATIONS

This application is based upon and claims the benefit of priority from prior Japanese Patent Applications No. 2007-181308, filed Jul. 10, 2007; and No. 2008-125121, filed May 12, 2008, the entire contents of both of which are incorporated herein by reference.

BACKGROUND OF THE INVENTION

1. Field of the Invention

The present invention relates to an X-ray computed tomography apparatus which can perform cone beam reconstruction, reconstruction processing apparatus, and image processing apparatus.

2. Description of the Related Art

There is an X-ray computed tomography apparatus (cone beam CT apparatus) which generates volume data by performing reconstruction of the projection data acquired by scanning a subject to be examined with cone beam X-rays. In cone beam CT, cone beam reconstruction such as FDK reconstruction (Feldkamp reconstruction) is useful.

Recently, with an increase in the number of element rows of an X-ray detector, the cone angle has increased. Owing to the influence of the cone angle, cone beam artifacts noticeably appear in the volume data generated on the basis of cone beam reconstruction.

CT scanning includes circular orbit scanning and helical scanning. The following problems arise in the respective scanning techniques.

(Circular Orbit Scanning)

Circular orbit scanning cannot acquire enough projection data required to obtain a complete solution. Line+Circle scanning is an application of circular orbit scanning. Line+Circle scanning can acquire enough projection data required to obtain a complete solution. However, Line+Circle scanning requires additional scanning. Additional scanning has the following problem. That is, to satisfy the reconstruction principle, the state of a subject in additional scanning needs to coincide with that in main scanning before additional scanning. More specifically, a change in contrast medium concentration and the body movement of the subject must not occur during main scanning and additional scanning. In practice, it is very difficult to satisfy this requirement. In addition, additional scanning complicates the workflow. Furthermore, additional scanning increases the dose to the subject.

(Helical Scanning)

Helical scanning can acquire enough projection data required to obtain a complete solution. Owing to the influence of the cone angle, however, noticeable cone beam artifacts appear in the volume data generated by directly performing cone beam reconstruction of the acquired projection data. Using the reconstruction method proposed by Alexander Katsevich in 2003 can obtain a complete solution on the basis of the projection data acquired by helical scanning. The reconstruction method by Katsevich is however limited in terms of helical pitch.

BRIEF SUMMARY OF THE INVENTION

It is an object of the present invention to provide an X-ray computed tomography apparatus, reconstruction processing apparatus, and image processing apparatus which can approximately reduce cone beam artifacts.

According to a first aspect of the present invention, there is provided an X-ray computed tomography apparatus comprising: a scanning unit which includes an X-ray tube and an X-ray detector for scanning a subject to be examined with cone beam X-rays; a reconstruction unit which generates first image data on the basis of output data from the canning unit; an extraction unit which extracts a cone beam artifact component contained in the first image data, on the basis of a typical shape and typical direction of the cone beam artifact; and a subtraction unit which generates second image data with the reduced cone beam artifact by subtracting the cone beam artifact component from the first image data.

According to a second aspect of the present invention, there is provided a reconstruction processing apparatus comprising: a storage unit which stores projection data acquired by scanning a subject to be examined with cone beam X-rays; a reconstruction unit which generates first image data on the basis of the projection data; an extraction unit which extracts a cone beam artifact component contained in the generated first image data on the basis of a typical shape and a typical direction of the cone beam artifact; and a subtraction unit which generates second image data with the reduced cone beam artifact component by subtracting the extracted cone beam artifact from the first image data.

According to a third aspect of the present invention, there is provided an image processing apparatus comprising: a storage unit which stores first image data generated on the basis of projection data acquired by scanning a subject to be examined with cone beam X-rays; an extraction unit which extracts a cone beam artifact component contained in the first image data on the basis of a typical shape and typical direction of the cone beam artifact; and a subtraction unit which generates second image data with the reduced cone beam artifact component by subtracting the extracted cone beam artifact component from the first image data.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a view showing the arrangement of an X-ray detector in FIG. 1;

FIG. 3 is a view showing cone beam artifacts according to the first embodiment;

DETAILED DESCRIPTION OF THE INVENTION

An X-ray CT apparatus (X-ray computed tomography apparatus), reconstruction processing apparatus, and image processing apparatus according to an embodiment of the present invention will be described below with reference to the views of the accompanying drawing.

First Embodiment

Figure 1:
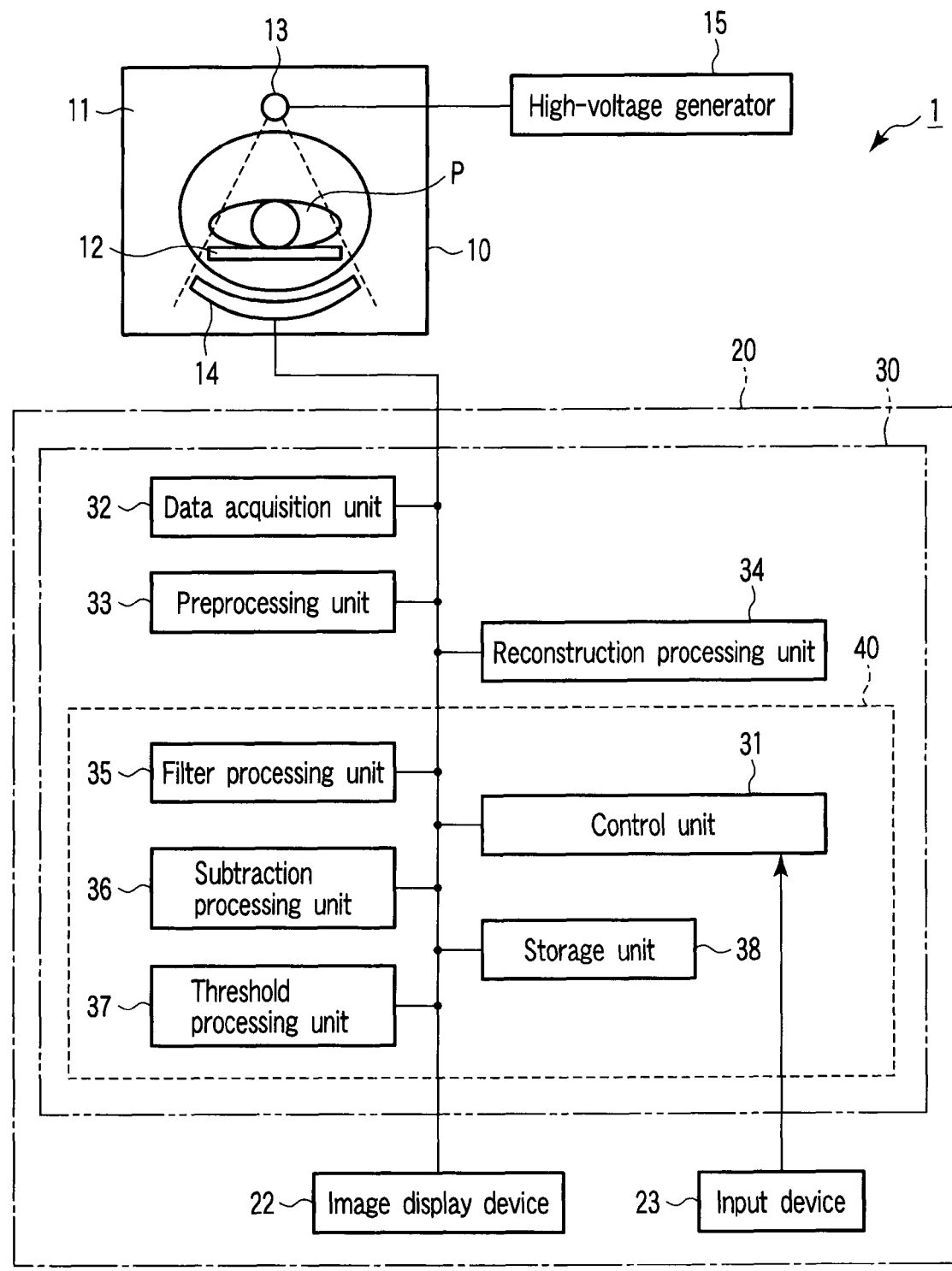
FIG. 1 is a block diagram showing the arrangement of an X-ray computed tomography apparatus according to the first embodiment of the present invention.

FIG. 1 is a block diagram showing the arrangement of an X-ray CT apparatus 1 according to the first embodiment. As shown in FIG. 1, the X-ray CT apparatus 1 comprises a gantry 10 and a computer device 20. The gantry 10 rotationally supports an annular or disk-like rotating frame 11. The rotating frame 11 has an X-ray tube 13 and an X-ray detector 14 which face each other through a subject P to be examined to scan the subject P. The rotating frame 11 continuously rotates at a predetermined angular velocity. In this case, the body axis of the subject P is defined as a Z-axis, a vertical axis is defined as a Y-axis, and an axis perpendicular to the Z- and Y-axes is defined as an X-axis. Note that the subject P is placed in an imaging area such that the body axis (Z-axis) almost coincides with the major axis of a top 12.

The X-ray tube 13 generates cone beam X-rays upon receiving a high voltage from a high-voltage generator 15 and a filament current. The cone beam X-rays are an X-ray beam having a large cone angle. This beam generally has a quadrangular pyramid shape. As shown in FIG. 2, the X-ray detector 14 detects the cone beam X-rays generated from an X-ray focal point F of the X-ray tube 13. The X-ray detector 14 has a plurality of X-ray detection elements 14a densely distributed in both the channel direction and the row direction. In other words, the X-ray detector 14 has a plurality of X-ray detection element rows 14R arrayed along the row direction (Z-axis). Each X-ray detection element row 14R has the plurality of X-ray detection elements 14a arrayed along the channel direction. Assume that the number of X-ray detection element rows of the X-ray detector 14 (the number of X-ray detection element rows 14R) is 64 or more. The spread angles of cone beam X-rays in the channel direction and the row direction are respectively called a fan angle $\gamma$ and a cone angle $\alpha$.

The computer device 20 comprises a reconstruction processing apparatus 30, an image display device 22 which displays an image, and an input device 23 which inputs various instructions from a user to the computer device 20. The reconstruction processing apparatus 30 includes a control unit 31 functioning as a central unit, a data acquisition unit (DAS) 32, a preprocessing unit 33, a reconstruction processing unit 34, a filter processing unit 35, a subtraction processing unit 36, a threshold processing unit 37, and a storage unit 38.

The data acquisition unit 32 converts a signal corresponding to the intensity of transmitted X-rays output from each channel of the X-ray detector 14 into a digital signal. This digital signal is called raw data. The preprocessing unit 33 preprocesses the raw data output from the data acquisition unit 32 to convert the data into projection data.

The reconstruction processing unit 34 generates image data by performing cone beam reconstruction, i.e., back projection processing, of the projection data in consideration of the cone angle. This image data may be multislice image data or volume data. For the sake of a concrete description to be made below, assume that image data in this embodiment is volume data. Cone beam reconstruction is performed in consideration of the cone angle of an X-ray path in the body axis direction (Z-axis direction) of the subject P. As described above, the number of element rows of the X-ray detector 14 is 64 or more, and hence the cone angle is large. For this reason, cone beam artifacts due to the large cone angle appear in generated volume data. The details of cone beam artifacts will be described later.

The filter processing unit 35 performs filtering, e.g., low-pass filtering of removing high-frequency components or high-pass filtering of removing low-frequency components, for projection data or volume data. It suffices to perform filtering in either a real space or in a frequency space. The filter processing unit 35 performs filtering of various types of data with respect to the X-, Y-, and Z-axes or planes defined by them. A concrete example of filtering in a real space is moving average processing of projection data, i.e., low-pass filtering in the Z direction. The filter processing unit 35 also performs Gauss filtering on an X-Y plane, i.e., low-pass filtering on an X-Y plane.

The subtraction processing unit 36 performs subtraction processing of volume data. The threshold processing unit 37 performs threshold processing of volume data. The storage unit 38 stores projection data and volume data.

The control unit 31 performs scanning using cone beam X-rays by controlling the respective constituent elements of the X-ray CT apparatus 1. The control unit 31 also performs cone beam artifact reduction processing of reducing cone beam artifact components contained in volume data by controlling the respective constituent elements of the reconstruction processing apparatus 30. Note that in this embodiment, the type of scanning orbit to be used is not specifically limited. That is, this embodiment can be applied to circular orbit scanning in which the top 12 is not moved during scanning, constant-velocity helical scanning in which the top 12 is moved at a constant velocity during scanning under the control of the control unit 31, and variable-velocity helical scanning in which the velocity of the top 12 is changed.

Cone beam artifact reduction processing will be described below. The typical shape and direction of a cone beam artifact will be described first.

More specifically, a cone beam artifact noticeably appears in a sagittal section image of the backbone (spinal column) of the subject. The backbone has vertebrae and intervertebral disks alternately arrayed along the body axis (Z-axis). A vertebra comprises a vertebral arch and a centrum. An intervertebral arch has a semi-annular shape. A centrum has a disk-like shape and is thin along the body axis. A centrum has a linear shape relative to a sagittal section. Since there is a steep CT value gradient between a centrum and its surrounding portion, a cone beam artifact appears from the centrum.

FIG. 3 is a view showing a sagittal section image on which cone beam artifacts CA extending from the two ends of a centrum CR. As shown in FIG. 3, the cone beam artifacts CA are artifacts which are narrow in the Z direction and wide in the X-Y direction. In other words, the cone beam artifacts CA have steep CT value gradients in the Z direction and moderate CT value gradients in the X-Y direction. That is, projection data and volume data containing the cone beam artifacts CA have high-frequency components in the Z direction.

Note that cone beam artifacts not only appear from centra of the backbone but also appear noticeably in edge components of linear regions of the lungs (e.g., vaculatures). That is, this embodiment can be applied to projection data and volume data containing cone beam artifact components. However, regions to be imaged are not limited.

The operation of cone beam artifact reduction processing of reducing cone beam artifact components having the above typical shape and typical direction, which is performed by the control unit 31, will be described next. Cone beam artifact reduction processing according to this embodiment roughly includes two types of processing. First cone beam artifact reduction processing A is a method of processing projection data and volume data acquired by cone beam X-rays. Second cone beam artifact reduction processing B is a method of processing only volume data without processing any projection data.

Figure 4:
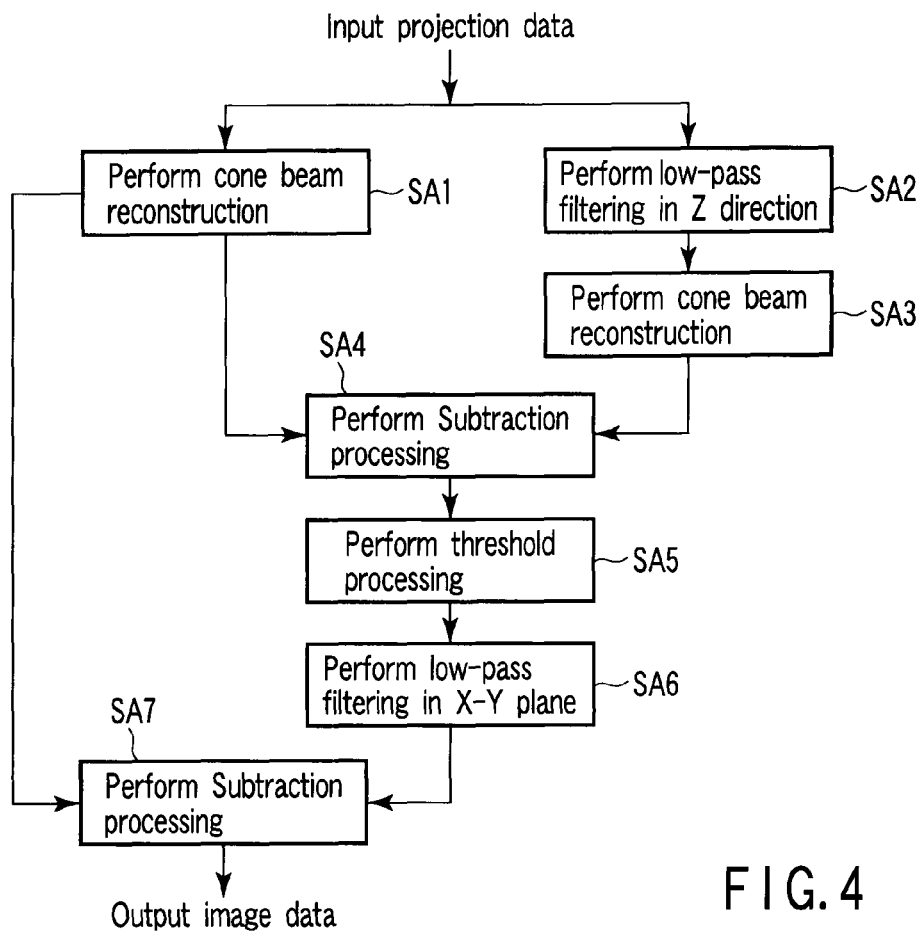
FIG. 4 is a flowchart showing the sequence of cone beam artifact reduction processing A performed under the control of a control unit in FIG. 1.

The operation of the first cone beam artifact reduction processing A will be described first with reference to FIG. 4. First of all, projection data is acquired by scanning with cone beam X-rays having a large cone angle under the control of the control unit 31. The projection data is temporarily stored in the storage unit 38. Upon receiving a request to start processing A from the user via the input device 23 or automatically after the acquisition of the projection data, the control unit 31 starts processing A.

Upon starting processing A, the control unit 31 sends the projection data to the reconstruction processing unit 34 and causes it to perform first reconstruction. In the first reconstruction, the reconstruction processing unit 34 generates volume data (to be referred to as reference volume data hereinafter) by cone beam reconstruction (step SA1). More specifically, FDK reconstruction is used as cone beam reconstruction. Reference volume data contains cone beam artifact components in addition to the living body components of the subject P.

The control unit 31 also causes the filter processing unit 35 to perform first low-pass filtering independently of step SA1. In the first low-pass filtering, the filter processing unit 35 performs low-pass filtering (typically, moving average processing) for the projection data in the Z direction (row direction/body axis direction) to remove high-frequency components from the projection data in the Z direction (step SA2). More specifically, the filter processing unit 35 extracts projection data on a projection path along the Z-axis. The filter processing unit 35 performs low-pass filtering for the extracted projection data in the Z direction.

After the first low-pass filtering processing, the control unit 31 causes the reconstruction processing unit 34 to perform the second reconstruction. In the second reconstruction, the reconstruction processing unit 34 generates volume data (to be referred to as first intermediate volume data hereinafter) by performing cone beam reconstruction of the projection data having undergone the low-pass filtering in the Z direction (step SA3). The intermediate volume data is volume data with the CT value gradients of cone beam artifact components and living body components in the Z direction being suppressed (blurred). The intermediate volume data is stored in the storage unit 38.

When the reference volume data and the first intermediate volume data are generated, the control unit 31 causes the subtraction processing unit 36 to perform first subtraction processing. In the first subtraction processing, the subtraction processing unit 36 generates difference volume data by subtracting the first intermediate volume data from the reference volume data (step SA4). The difference volume data comprises an edge component in the Z direction (a component having a steep CT value gradient). More specifically, an edge component in the Z direction is an edge component of a cone beam artifact, an edge component between living body tissues, or noise in the Z direction. Note that in subtraction processing, it suffices to adjust the degree of subtraction by multiplying the reference volume data and the first intermediate volume data by weighting factors. The difference volume data is stored in the storage unit 38.

After the first subtraction processing, the control unit 31 causes the threshold processing unit 37 to perform threshold processing. In the threshold processing, the threshold processing unit 37 performs threshold processing for the difference volume data by using the CT value of a cone beam artifact component as a threshold (step SA5). With the threshold processing, a component having a CT value equal to that of the cone beam artifact is left in the difference volume data.

More specifically, first of all, the threshold processing unit 37 sets the range of CT values which cone beam artifacts have (e.g., the range between the maximum and minimum CT values of cone beam artifact components). The CT values of most living body components fall outside the set CT value range. The threshold processing unit 37 replaces CT values falling outside the set CT value range by zero values. The difference volume data after the threshold processing has a steep CT value gradient in the Z direction and contains a component having a CT value equal to that of a cone beam artifact component. In other words, the difference volume data has an edge component in the Z direction which has a CT value equal to that of a cone beam artifact component. Note that a CT value range can be set before threshold processing.

After the threshold processing, the control unit 31 causes the filter processing unit 35 to perform the second low-pass filtering. In the second low-pass filtering, the filter processing unit 35 performs low-pass filtering (more specifically, two-dimensional Gaussian filtering) for the difference volume data in the X-Y plane after the threshold processing (step SA6). The difference volume data having undergone the low-pass filtering in the X-Y plane will be referred to as false image component volume data. The low-pass filtering in the X-Y plane suppresses (blurs) a component which is contained in the difference volume data and has a steep CT value gradient in the X-Y plane. A cone beam artifact component has a spread in the X-Y plane. For this reason, even if low-pass filtering is performed for a cone beam artifact component in the X-Y plane, only the CT value gradients of edge components of a cone beam artifact and living body component in the X-Y plane are suppressed. Therefore, after the low-pass filtering in the X-Y plane, most of cone beam artifact components are left without being suppressed. That is, the false image component volume data is the difference volume data from which cone beam artifact components have been extracted by suppressing living body components. The false image component volume data is stored in the storage unit 38.

After the second low-pass filtering, the control unit 31 causes the subtraction processing unit 36 to perform the second subtraction processing. In the second subtraction processing, the subtraction processing unit 36 generates volume data (to be referred to as the first resultant volume data hereinafter) by subtracting the false image volume data from the reference volume data (step SA7). As described above, reference volume data contains cone beam artifact components and living body components. False image component volume data contains no living body components but contains cone beam artifact components. Therefore, the first resultant volume data is volume data in which cone beam artifact components are reduced. The generated first resultant volume data is output.

With the above operation, the cone beam artifact reduction processing A is terminated. In the cone beam artifact reduction processing A, the X-ray CT apparatus 1 generates the first resultant volume data with reduced cone beam artifact components by subtracting the false image component volume data comprising cone beam artifact components from the reference volume data containing the cone beam artifact components. Processing A requires no additional scanning unlike Line+Circle scanning. In addition, this processing neither requires complicated calculation nor has any limitation in terms of helical pitch unlike the reconstruction method by Katsevich. Processing A can therefore approximately reduce cone beam artifact components regardless of the scanning orbit.

Figure 5:
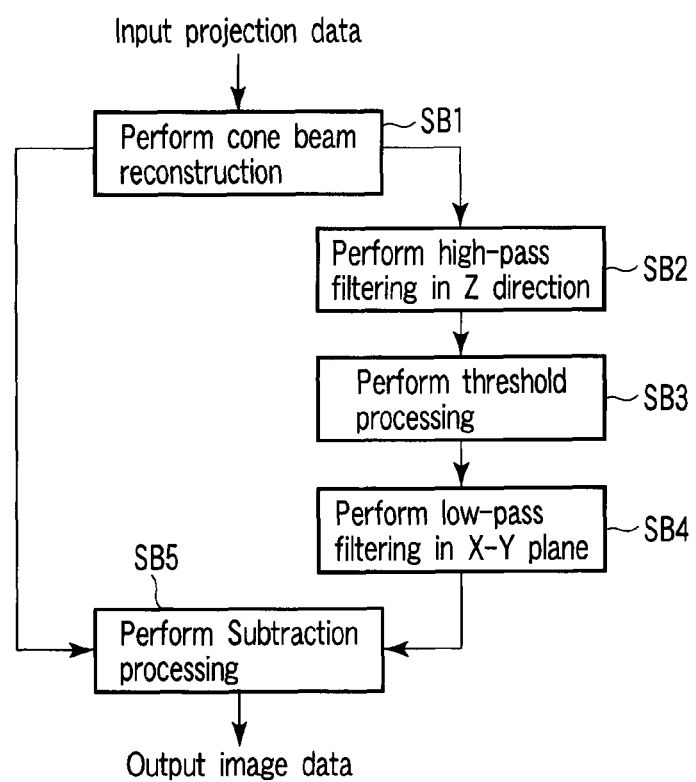
FIG. 5 is a flowchart showing the sequence of cone beam artifact reduction processing B performed under the control of the control unit in FIG. 2.

The operation of the cone beam artifact reduction processing B will be described next with reference to FIG. 5. Projection data is acquired by scanning with cone beam X-rays having a large cone angle. Upon receiving a request to start processing B from the user via the input device 23 or automatically, the control unit 31 starts processing B. When processing B starts, the control unit 31 sends the acquired projection data to the reconstruction processing unit 34 and causes it to perform cone beam reconstruction. In the cone beam reconstruction, the reconstruction processing unit 34 generates reference volume data (step SB1). The generated reference volume data is stored in the storage unit 38.

After FDK reconstruction, the control unit 31 causes the filter processing unit 35 to perform high-pass filtering. In the high-pass filtering, the filter processing unit 35 generates volume data (to be referred to as the second intermediate volume data hereinafter) with enhanced CT value gradient components in the Z direction, which are contained in cone beam artifact components and living body components contained in the reference volume data, by performing high-pass filtering for the reference volume data in the Z direction. That is, the second intermediate volume data contains edge components of cone beam artifacts, edge components between living body tissues, noise, and the like in the Z direction. Note that in this processing, high-pass filtering is performed in the Z direction, but this operation can be replaced by another method. For example, it is possible to obtain the same result as that described above by performing low-pass filtering for reference volume data in the Z direction and subtracting the reference volume data having undergone low-pass filtering from the original reference volume data. The second intermediate volume data is stored in the storage unit 38.

After the high-pass filtering, the control unit 31 causes the threshold processing unit 37 to perform threshold processing. In the threshold processing, the threshold processing unit 37 performs threshold processing for the second intermediate volume data by using the CT value of a cone beam artifact component as a threshold (step SB3). After the threshold processing, the second intermediate volume data contains a component having a steep CT value gradient in the Z direction and a CT value equal to that of a cone beam artifact component. In other words, the second intermediate volume data has an edge component in the Z direction which has a CT value equal to that of a cone beam artifact component.

After the threshold processing, the control unit 31 causes the filter processing unit 35 to perform low-pass filtering. In the low-pass filtering, the filter processing unit 35 performs low-pass filtering (more specifically, two-dimensional Gaussian filtering) for the second intermediate volume data in the X-Y plane after the threshold processing (step SB4). After the low-pass filtering in the X-Y plane, false image component volume data is generated. Performing low-pass filtering in the X-Y plane suppresses components which are contained in the second intermediate volume data and have steep CT value gradients in the X-Y plane. The false image component volume data is volume data with cone beam artifact components enhanced by suppressing living body components in the second intermediate volume data. The false image component volume data is stored in the storage unit 38.

After the low-pass filtering, the control unit 31 causes the subtraction processing unit 36 to perform subtraction processing. In the subtraction processing, the subtraction processing unit 36 generates second resultant volume data by subtracting the false image component volume data from the reference volume data (step SB5). The second resultant volume data is volume data with reduced cone beam artifact components. The second resultant volume data is output.

The cone beam artifact reduction processing B can reduce cone beam artifact components contained in volume data by processing only the volume data generated by reconstruction. In addition, as compared with the cone beam artifact reduction processing A, processing B shortens the time required for processing for reducing cone beam artifacts because of a smaller number of times of reconstruction.

The first embodiment can therefore approximately reduce cone beam artifacts. In addition, since the processing in this method is relatively simple, cone beam artifacts can be reduced in a short processing time.

Note that the first embodiment is not limited to the above arrangement. This embodiment can be implemented by an image processing apparatus 40 comprising a control unit 31 functioning as a central unit, a filter processing unit 35, a subtraction processing unit 36, a threshold processing unit 37, and a storage unit 38. In this case, the storage unit 38 stores the reference volume data, difference volume data, and second intermediate volume data generated by the X-ray CT apparatus 1, the reconstruction processing apparatus 30, and the like. For example, the control unit 31 controls the respective constituent elements of the image processing apparatus 40 to perform steps SB2 to SB5 in the cone beam artifact reduction processing B. As a result, volume data with reduced cone beam artifacts are generated by performing only simple image processing for the reference volume data containing cone beam artifacts, e.g., filter processing, threshold processing, or subtraction processing.

The order of the respective steps in the cone beam artifact reduction processing A and B is not limited to that described above. For example, steps SA5 and SA6 or steps SB3 and SB4 can be interchanged. In step SA2, low-pass filtering is performed for projection data in the Z direction. However, it suffices to generate difference volume data by performing low-pass filtering for reference volume data in the Z direction and subtracting the unprocessed reference volume data from the reference volume data having undergone the low-pass filtering in the Z direction. In this case, no processing other than cone beam reconstruction is performed for projection data, and only volume data is processed.

Although the precision in extracting cone beam artifact components deteriorates, it suffices to omit the threshold processing in step SA5 or step SB3 in order to shorten the processing time. In addition, it suffices to use the output in step SA4 in FIG. 4 as an artifact component and omit the processing in step SA5 or step SA6.

Second Embodiment

In principle, cone beam artifacts gradually decrease in intensity toward the middle element row of an X-ray detector 14, at which the cone angle is small, and gradually increase toward the end element rows of the X-ray detector 14, at which the cone angle is large. An X-ray CT apparatus according to the second embodiment uses this characteristic to improve the cone beam artifact reduction precision, thereby improving the image quality of resultant volume data.

The X-ray CT apparatus according to the second embodiment will be described below. Note that the same reference numbers denote constituent elements having substantially the same functions as in the first embodiment, and a repetitive description will be made only when required.

Figure 6:
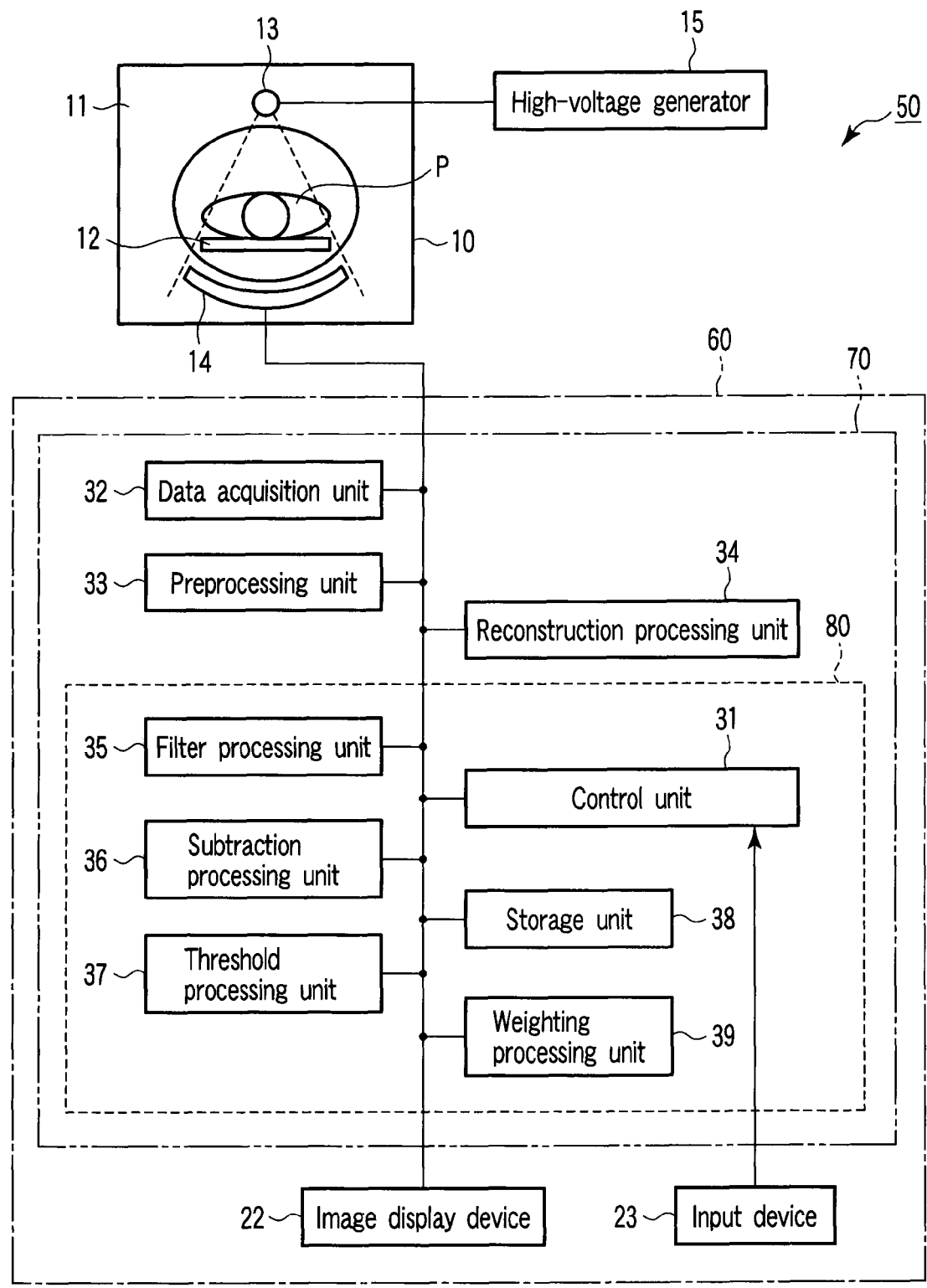
FIG. 6 is a block diagram showing the arrangement of an X-ray computed tomography apparatus according to the second embodiment of the present invention.

FIG. 6 is a block diagram showing the arrangement of an X-ray CT apparatus 50 according to the second embodiment of the present invention. As shown in FIG. 6, the X-ray CT apparatus 50 comprises a gantry 10 and a computer device 60. The computer device 60 comprises a reconstruction processing apparatus 70, an image display device 22 which displays an image, and an input device 23 which inputs various instructions from a user to the computer device 60. The reconstruction processing apparatus 70 includes a control unit 31 functioning as a central unit, a data acquisition unit (DAS) 32, a preprocessing unit 33, a reconstruction processing unit 34, a filter processing unit 35, a difference processing unit 36, a threshold processing unit 37, a storage unit 38, and a weighting processing unit 39.

The weighting processing unit 39 performs weighting with the distribution of weights changing in accordance with positions in the Z direction for extracted cone beam artifact components.

The operation of cone beam artifact reduction processing according to the second embodiment which is performed by the control unit 31 will be described below. The cone beam artifact reduction processing according to the second embodiment roughly includes two types of processing. First cone beam artifact reduction processing C is performed for projection data acquired by cone beam X-rays and volume data. Second cone beam artifact reduction processing D is performed for only volume data but is not performed for projection data.

Figure 7:
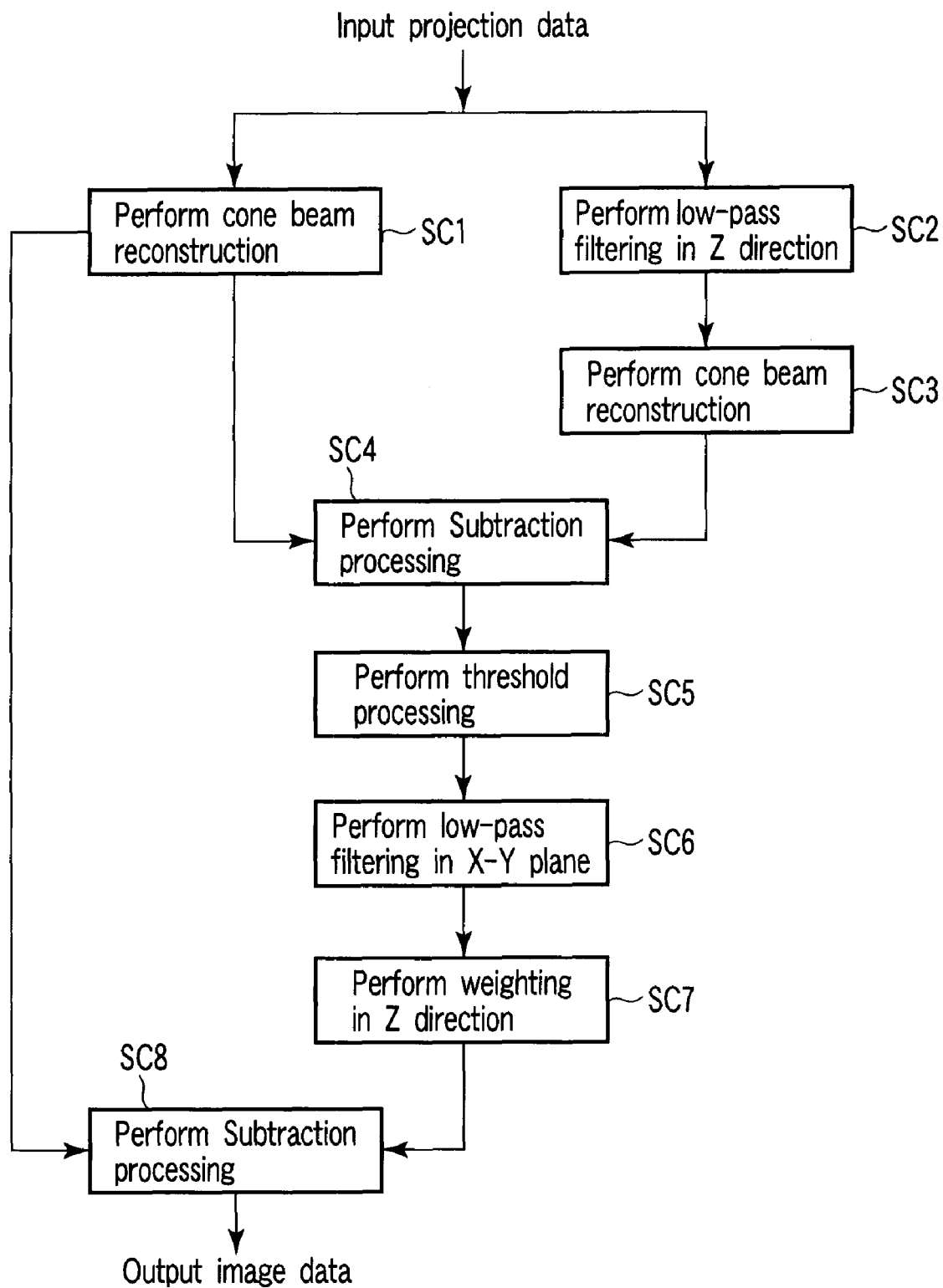
FIG. 7 is a flowchart showing the sequence of cone beam artifact reduction processing C performed under the control of the control unit FIG. 6.

Cone beam artifact reduction processing C will be described first. FIG. 7 is a flowchart showing the sequence of the cone beam artifact reduction processing C. First of all, projection data is acquired by scanning with cone beam X-rays having a large cone angle under the control of the control unit 31. The projection data is temporarily stored in the storage unit 38. Upon receiving a request to start processing C from the user via the input device 23 or automatically after the acquisition of the projection data, the control unit 31 starts processing C.

Upon starting processing C, the control unit 31 sends the projection data to the reconstruction processing unit 34 and causes it to perform first reconstruction. In the first reconstruction, the reconstruction processing unit 34 generates reference volume data by cone beam reconstruction (e.g., FDK reconstruction) (step SC1).

The control unit 31 also causes the filter processing unit 35 to perform first low-pass filtering independently of step SC1. In the first low-pass filtering, the filter processing unit 35 performs low-pass filtering (typically, moving average processing) for the projection data in the Z direction (column direction/body axis direction) to remove high-frequency components in the Z direction from the projection data (step SC2).

After the first low-pass filtering processing, the control unit 31 causes the reconstruction processing unit 34 to perform the second reconstruction. In the second reconstruction, the reconstruction processing unit 34 generates first intermediate volume data by performing cone beam reconstruction of the projection data having undergone the low-pass filtering in the Z direction (step SC3). The first intermediate volume data is stored in the storage unit 38.

When the reference volume data and the first intermediate volume data are generated, the control unit 31 causes the subtraction processing unit 36 to perform first subtraction processing. In the first subtraction processing, the subtraction processing unit 36 generates difference volume data by subtracting the first intermediate volume data from the reference volume data (step SC4). The difference volume data is stored in the storage unit 38.

After the first difference processing, the control unit 31 causes the threshold processing unit 37 to perform threshold processing. In the threshold processing, the threshold processing unit 37 performs threshold processing for the difference volume data by using the CT value of a cone beam artifact component as a threshold (step SC5).

After the threshold processing, the control unit 31 causes the filter processing unit 35 to perform the second low-pass filtering. In the second low-pass filtering, the filter processing unit 35 generates false image component volume data by performing low-pass filtering (more specifically, two-dimensional Gaussian filtering) for the difference volume data in the X-Y plane after the threshold processing (step SC6). The false image component volume data is stored in the storage unit 38.

After the second low-pass filtering, the control unit 31 causes the weighting processing unit 39 to perform weighting. In the weighting, the weighting processing unit 39 performs, for the false image component volume data, weighting with weights changing in accordance with positions on the volume data in the Z direction (positions in the row direction of the X-ray detector 14) (step SC7). More specifically, the gradient of the weighting distribution gradually increases from the center in the Z direction (the middle element row of the X-ray detector 14, with a small cone angle) to the edges (the end element rows of the X-ray detector 14, with a large cone angle). With this weighting, the distribution of cone beam artifact components in the false image component volume data becomes similar to the distribution of actual cone beam artifact components.

Figure 8:
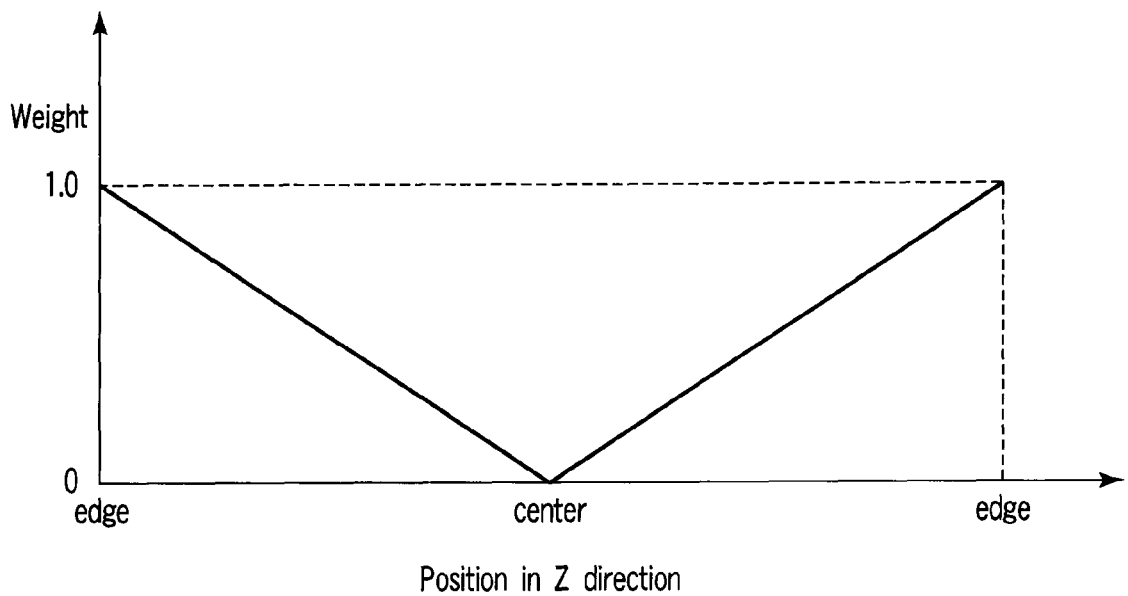
FIG. 8 is a graph showing an example of a weight distribution for weighting performed by a weighting processing unit in FIG. 6.

FIG. 8 is a graph showing an example of a weighting distribution. As shown in FIG. 8, weights linearly decrease from the edges to the center along the Z-axis. For example, the weight at the edge is 1.0. That is, the CT value of the cone beam artifact component at the edge is not changed. In contrast, the weight at the center is 0. That is, the CT value of the cone beam artifact component at the center becomes zero. Although the weights decrease linearly in the above case, the weights may change in the form of a curve. For example, as an example of a change in the form of a curve, a change in the form of a sigmoid curve is conceivable. That is, the weights change in the form of the letter S from the edges to the center.

After the weighting, the control unit 31 causes the second subtraction processing unit 36 to perform subtraction processing. In the second subtraction processing, the subtraction processing unit 36 generates third resultant volume data by subtracting the false image component volume data having undergone weighting from the reference volume data (step SC8). The third resultant volume data is obtained in consideration of a cone beam artifact component characteristic that generated components gradually decrease in intensity from the edges to the center in the Z direction. Therefore, excessive correction of cone beam artifact components which tends to occur at the center of the first or second resultant volume data does not easily occur in the third resultant volume data. That is, the third resultant volume data is higher in image quality at the center than the first resultant volume data and the second resultant volume data.

Note that the execution order of weighting is not limited to that described above. For example, this processing can be performed before step SC5 or step SC6.

Figure 9:
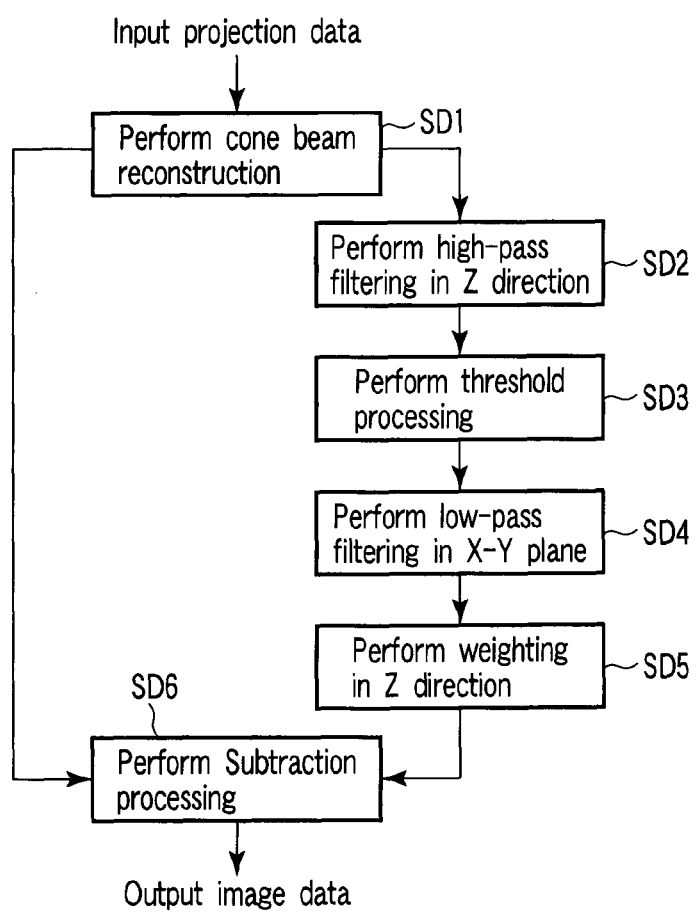
FIG. 9 is a flowchart showing the sequence of cone beam artifact reduction processing D performed under the control of the control unit in FIG. 6.

The cone beam artifact reduction processing D will be described next. FIG. 9 is a flowchart showing the sequence of the cone beam artifact reduction processing D.

Projection data is acquired by scanning with cone beam X-rays having a large cone angle. Upon receiving a request to start processing D from the user via the input device 23 or automatically, the control unit 31 starts processing D. When processing D starts, the control unit 31 sends the acquired projection data to the reconstruction processing unit 34 and causes it to perform cone beam reconstruction. In the cone beam reconstruction, the reconstruction processing unit 34 generates reference volume data (step SD1). The generated reference volume data is stored in the storage unit 38.

After cone beam reconstruction, the control unit 31 causes the filter processing unit 35 to perform high-pass filtering. In the high-pass filtering, the filter processing unit 35 generates second intermediate volume data with enhanced CT value gradient components in the Z direction, which are contained in cone beam artifact components and living body components contained in the reference volume data, by performing high-pass filtering for the reference volume data in the Z direction (step SD2). The second intermediate volume data is stored in the storage unit 38.

After the high-pass filtering, the control unit 31 causes the threshold processing unit 37 to perform threshold processing. In the threshold processing, the threshold processing unit 37 performs threshold processing for the second intermediate volume data by using the CT value of a cone beam artifact component as a threshold (step SD3). With the threshold processing, a component having a steep CT value gradient in the Z direction and a CT value equal to that of a cone beam artifact component is left in the second intermediate volume data.

After the threshold processing, the control unit 31 causes the filter processing unit 35 to perform low-pass filtering. In the low-pass filtering, the filter processing unit 35 performs low-pass filtering (more specifically, two-dimensional Gaussian filtering) for the second intermediate volume data in the X-Y plane after the threshold processing (step SD4). With the low-pass filtering in the X-Y plane, false image component volume data is generated. The false image component volume data is stored in the storage unit 38.

After the low-pass filtering, the control unit 31 causes the weighting processing unit 39 to perform weighting. In the weighting, the weighting processing unit 39 performs, for the false image component volume data, weighting with weights changing in accordance with positions on the volume data in the Z direction (step SD5).

After the weighting, the control unit 31 causes the subtraction processing unit 36 to perform subtraction processing. In the subtraction processing, the subtraction processing unit 36 generates fourth resultant volume data by subtracting the false image component volume data having undergone weighting from the reference volume data (step SD6).

According to the cone beam artifact reduction processing D, processing only the volume data generated by reconstruction can reduce cone beam artifact components contained in the volume data in consideration of the cone beam artifact characteristic that the generated artifacts gradually decrease in intensity from the edges to the center in the Z direction.

The second embodiment therefore can approximately reduce cone beam artifacts.

Note that the second embodiment is not limited to the above arrangement. This embodiment can also be implemented by an image processing apparatus 80 comprising a control unit 31 functioning as a central unit, a filter processing unit 35, a subtraction processing unit 36, a threshold processing unit 37, a storage unit 38, and a weighting processing unit 39. In this case, the storage unit 38 stores the reference volume data, difference volume data, and second intermediate volume data generated by the X-ray CT apparatus 50, the reconstruction processing apparatus 70, and the like. For example, the control unit 31 controls the respective constituent elements of the image processing apparatus 80 to perform steps SD2 to SD6 in the cone beam artifact reduction processing D. As a result, volume data with reduced cone beam artifacts are generated by performing only simple image processing for the reference volume data containing cone beam artifacts, e.g., filter processing, threshold processing, subtraction processing, and weighting processing.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomography apparatus comprising:
a scanning unit which includes an X-ray tube and an X-ray detector for scanning a subject to be examined with cone beam X-rays;
a reconstruction unit which generates first image data on the basis of output data from the scanning unit;
an extraction unit which extracts a cone beam artifact component contained in the first image data, on the basis of a typical shape and typical direction of the cone beam artifact; and
a subtraction unit which generates second image data with a reduced cone beam artifact by subtracting the cone beam artifact component from the first image data.

2. The apparatus according to claim 1, wherein the reconstruction unit generates the first image data by performing Feldkamp reconstruction of the output data.

3. The apparatus according to claim 1, wherein the extraction unit extracts the cone beam artifact component by performing filtering for at least one of the output data and the first image data.

4. The apparatus according to claim 1, wherein the extraction unit generates third image data comprising an edge component in a body axis direction of the subject as the cone beam artifact component on the basis of at least one of the output data and the first image data.

5. The apparatus according to claim 4, wherein the extraction unit performs low-pass filtering for the output data in the body axis direction, generates fourth image data on the basis of output data having undergone low-pass filtering in the body axis direction, and generates the third image data by subtracting the generated fourth image data from the first image data.

6. The apparatus according to claim 4, wherein the extraction unit generates the third image data by performing high-pass filtering for the first image data in the body axis direction.

7. The apparatus according to claim 1, wherein the extraction unit extracts the cone beam artifact component by suppressing an edge component in a plane substantially perpendicular to the body axis direction which is contained in third image data comprising the edge component in the body axis direction of the subject.

8. The apparatus according to claim 1, wherein the extraction unit extracts the cone beam artifact component by performing low-pass filtering in a plane substantially perpendicular to the body axis direction of the subject for third image data comprising an edge component in the body axis direction of the subject.

9. The apparatus according to claim 1, wherein the extraction unit extracts the cone beam artifact component by removing a living body component contained in third image data comprising an edge component in the body axis direction of the subject.

10. The apparatus according to claim 1, wherein the extraction unit extracts the cone beam artifact component by performing threshold processing for third image data comprising an edge component in the body axis direction of the subject on the basis of a pixel value which the cone beam artifact component has.

11. The apparatus according to claim 1, wherein the extraction unit performs low-pass filtering for the output data in the body axis direction of the subject, generates fourth image data on the basis of the output data having undergone low-pass filtering in the body axis direction, generates the third image data by subtracting the generated fourth image data from the first image data, and extracts the cone beam artifact component by performing low-pass filtering in a plane substantially perpendicular to the body axis direction for the generated third image data.

12. The apparatus according to claim 1, wherein the extraction unit generates fourth image data by performing high-pass filtering for the first image data in the body axis direction of the subject, generates the third image data by subtracting the generated fourth image data from the first image data, and extracts the cone beam artifact component by performing low-pass filtering in a plane substantially perpendicular to the body axis direction for the generated third image data.

13. The apparatus according to claim 1, further comprising a weighting processing unit which performs weighting with a distribution of weights changing in accordance with positions in the body axis direction for the cone beam artifact component.

14. The apparatus according to claim 13, wherein the weighting processing unit performs the weighting with the distribution of weights gradually increasing from a center to edges in the body axis direction.

15. The apparatus according to claim 1, wherein the X-ray detector includes not less than 64 X-ray detection element rows arrayed along the body axis direction of the subject.

16. A reconstruction processing apparatus comprising:
a storage unit which stores projection data acquired by scanning a subject to be examined with cone beam X-rays;
a reconstruction unit which generates first image data on the basis of the projection data;
an extraction unit which extracts a cone beam artifact component contained in the generated first image data on the basis of a typical shape and a typical direction of the cone beam artifact; and
a subtraction unit which generates second image data with a reduced cone beam artifact component by subtracting the extracted cone beam artifact from the first image data.

17. An image processing apparatus comprising:
a storage unit which stores first image data generated on the basis of projection data acquired by scanning a subject to be examined with cone beam X-rays;
an extraction unit which extracts a cone beam artifact component contained in the first image data on the basis of a typical shape and typical direction of the cone beam artifact; and
a subtraction unit which generates second image data with a reduced cone beam artifact component by subtracting the extracted cone beam artifact component from the first image data.

* * * * *